United States Patent
Xu et al.

(10) Patent No.: US 11,299,680 B1
(45) Date of Patent: Apr. 12, 2022

(54) CATALYTIC CRACKING OF GLYCERIDE OILS WITH PHOSPHORUS-CONTAINING ZSM-5 LIGHT OLEFINS ADDITIVES

(71) Applicant: Chevron U.S.A. Inc., San Ramon, CA (US)

(72) Inventors: Mingting Xu, Walnut Creek, CA (US); Tengfei Liu, Fairfield, CA (US); Richard L. Grove, Spanish Fort, AL (US); Michael K. Maholland, Park City, UT (US)

(73) Assignee: CHEVRON U.S.A. INC., San Ramon, CA (US)

( * ) Notice: Subject to any disclaimer, the term of this patent is extended or adjusted under 35 U.S.C. 154(b) by 0 days.

(21) Appl. No.: 17/356,691

(22) Filed: Jun. 24, 2021

Related U.S. Application Data

(60) Provisional application No. 63/119,715, filed on Dec. 1, 2020.

(51) Int. Cl.
| | | |
|---|---|---|
| *C10G 3/00* | (2006.01) | |
| *C07C 1/22* | (2006.01) | |
| *B01J 29/40* | (2006.01) | |
| *B01J 29/70* | (2006.01) | |
| *B01J 29/08* | (2006.01) | |
| *B01J 29/80* | (2006.01) | |

(52) U.S. Cl.
CPC ............... *C10G 3/49* (2013.01); *B01J 29/08* (2013.01); *B01J 29/40* (2013.01); *B01J 29/70* (2013.01); *B01J 29/80* (2013.01); *C07C 1/22* (2013.01); *C10G 3/57* (2013.01); *C07C 2529/08* (2013.01); *C07C 2529/40* (2013.01); *C07C 2529/70* (2013.01); *C10G 2300/1007* (2013.01); *C10G 2300/1014* (2013.01); *C10G 2300/1018* (2013.01); *C10G 2300/4006* (2013.01); *C10G 2300/4012* (2013.01); *C10G 2300/70* (2013.01); *C10G 2400/02* (2013.01); *C10G 2400/20* (2013.01)

(58) Field of Classification Search
CPC .... C10G 3/49; C10G 3/57; C10G 2300/1007; C10G 2300/1014; C10G 2300/1018; C10G 2300/4006; C10G 2300/4012; C10G 2300/70; C10G 2400/02; C10G 2400/20; B01J 29/08; B01J 29/40; B01J 29/70; B01J 29/80; C07C 1/22; C07C 2529/08; C07C 2529/40; C07C 2529/70
See application file for complete search history.

(56) References Cited

U.S. PATENT DOCUMENTS

| | | | |
|---|---|---|---|
| 2012/0292230 A1* | 11/2012 | Long | B01J 29/46 208/114 |
| 2013/0289324 A1* | 10/2013 | Price | B01J 29/084 585/469 |

FOREIGN PATENT DOCUMENTS

WO    2012142490 A2    10/2012

OTHER PUBLICATIONS

J.C. Vedrine, A. Aroux, P. Dejaifve, V. Ducarme, H. Hoser and S. Zhou "Catalytic and Physical Properties of Phosphorus-Modified ZSM-5 Zeolite" J. Catal. 1982, 73, 147-160.

(Continued)

*Primary Examiner* — Thuan D Dang

(57) ABSTRACT

A process is provided for the catalytic cracking of a glyceride oil feedstock with a catalyst composition containing a phosphorus-containing ZSM-5 light olefins additive.

6 Claims, 1 Drawing Sheet

(56) References Cited

OTHER PUBLICATIONS

R.O. Idem, S.P.R. Katikaneni and N.N. Bakhshi "Catalytic conversion of canola oil to fuels and chemicals: roles of catalyst acidity, basicity and shape selectivity on product distribution" Fuel Process. Technol. 1997, 51, 101-125.

F A. Twaiq, N.A.M. Zabidi and S.Bhatia "Catalytic Conversion of Palm Oil to Hydrocarbons: Performance of Various Zeolite Catalysts" Ind. Eng. Chem. Res. 1999, 38, 3230-3237.

D. Chen, N.I. Tracy, D.W. Crunkleton and G.L. Price "Comparison of canola oil conversion over MFI, BEA, and FAU" Applied Catal. A 2010, 384, 206-212.

N. Rahimi and R. Karimzadeh "Catalytic cracking of hydrocarbons over modified ZSM-5 zeolites to produce light olefins: A review" Applied Catal. A 2011, 398, 1-17.

H.L Janardhan, G.V.Shanbhag and A.B. Halgeri "Shape-selective catalysis by phosphate modified ZSM-5: Generation of new acid sites with pore narrowing" Applied Catal. A 2014, 471, 12-18.

H.X. Vu, M. Schneider, U. Bentrup, T.T. Dang, B.M.Q Phan, D.A. Nguyen, U. Armbruster and A. Martin "Hierarchical ZSM-5 Materials for an Enhanced Formation of Gasoline-Range Hydrocarbons and Light Olefins in Catalytic Cracking of Triglyceride-Rich Biomass" Ind. Eng. Chem. Res. 2015, 54, 1773-1782.

X. Zhao, L. Wei, J. Julson, Q.Qiao, A. Dubey and G. Anderson "Catalytic cracking of non-edible sunflower oil over ZSM-5 for hydrocarbon bio-jet fuel" New Biotechnol. 2015, 32, 300-312.

V.P Doronin, P.V. Lipin, O.V. Potapenko, V.V. Vysotsky, T.I. Gulyaeva and T.P.Sorokina "Modification of ZSM-5 Zeolite in order to Improve the Yield of Light Olefins during Cracking of Oil and Plant Materials" Kataliz v promyshlennosti 2018;18, 31-40.

\* cited by examiner

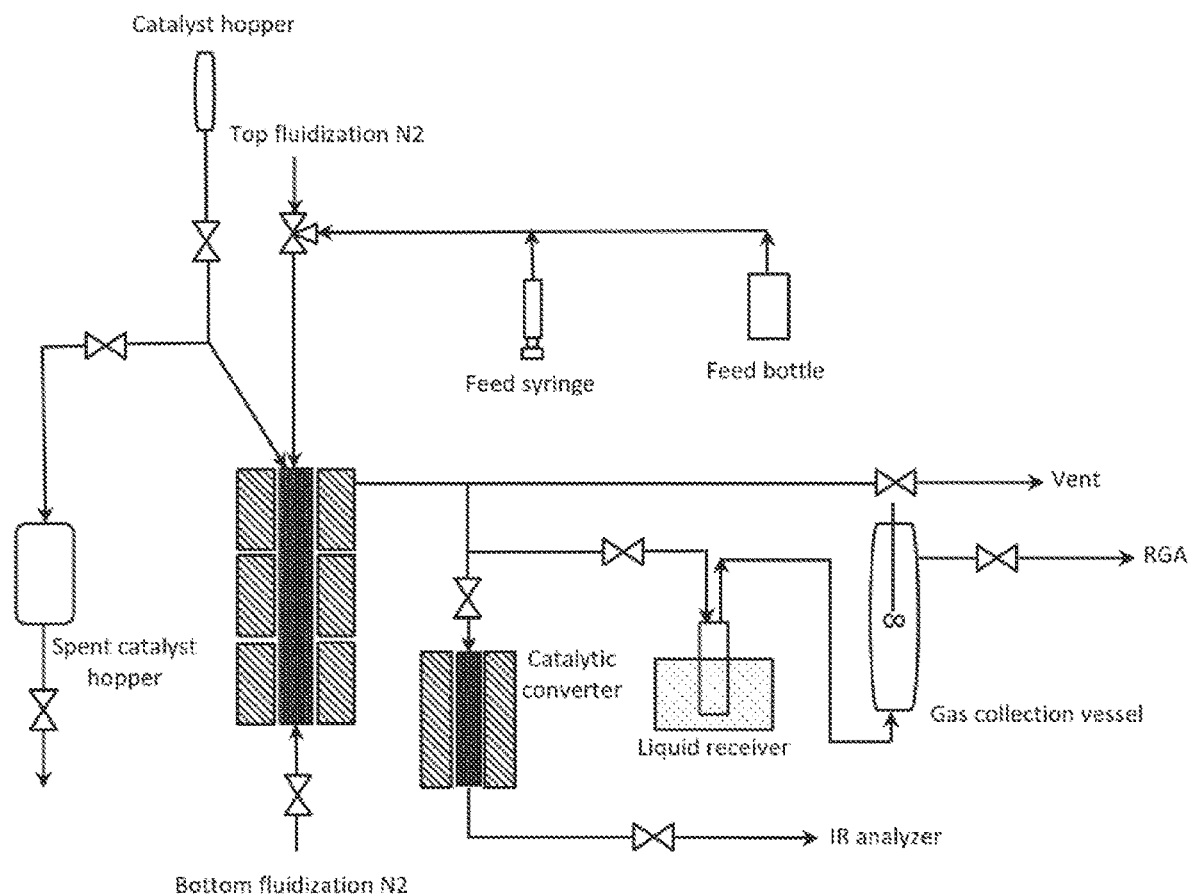

US 11,299,680 B1

CATALYTIC CRACKING OF GLYCERIDE OILS WITH PHOSPHORUS-CONTAINING ZSM-5 LIGHT OLEFINS ADDITIVES

FIELD

This disclosure relates to the catalytic cracking of glyceride oils and more particularly to the catalytic cracking of triglyceride materials using a phosphorus-containing ZSM-5 light olefins additive as catalyst.

BACKGROUND

Catalytic cracking, and particularly fluidized catalytic cracking (FCC), is routinely used to convert heavy hydrocarbon feedstocks to lighter products, such as gasoline and distillate range fractions. Additionally, there is an ever increasing need to enhance the yield of petrochemical building blocks such as propylene, ethylene, and aromatics (benzene, toluene, xylenes, etc.) in the product slate from catalytic cracking processes.

FCC catalysts are often blends of a catalytically active large-pore zeolite component (e.g., FAU framework type zeolite) and additives containing other zeolites. These catalysts typically have a crystalline zeolite content of about 10 to about 50 wt. % with the rest being matrix or diluent. The large-pore component catalyzes the breakdown of primary products from the catalytic cracking reaction into clean products such as naphtha and distillates for fuels and olefins for chemical feedstocks. Conventional additives often contain phosphorus-activated ZSM-5, a medium-pore zeolite, which selectively converts primary cracking products (e.g., gasoline olefins) to C3 and C4 olefins and improves gasoline octanes. Improvement of the activity or the selectivity with phosphorus is known to increase the effectiveness of ZSM-5. Additives to the FCC process usually amount to no more than 10% of the total catalyst.

To reduce dependence on fossil fuels, it is desirable to produce fuels and other useful materials from renewable resources, such as natural oils. The natural oils contain mostly glycerides, and in particular, triglycerides. While natural oils are amenable to catalytic cracking, the yields and product distributions are less than desired when using conventional catalysts such as the commercial FCC catalysts.

According to the present disclosure, it has now been found phosphorus-containing ZSM-5 based light olefins additives can be used as a base catalyst for catalytic cracking of renewable feedstocks, exhibiting surprisingly high yields of light olefins and aromatics-enriched naphtha, as well improving the octane of the gasoline fraction relative to conventional large-pore FCC catalysts.

SUMMARY

In one aspect, there is provided a process for catalytic cracking of a glyceride oil, the process comprising: (a) contacting the glyceride oil with a cracking catalyst comprising at least 80 wt. % of a phosphorus-containing ZSM-5 light olefins additive at catalytic cracking conditions to obtain a product stream comprising hydrocarbons; and (b) separating at least one hydrocarbon fraction from the product stream.

BRIEF DESCRIPTION OF THE DRAWINGS

FIG. 1 is a schematic diagram for an experimental setup in the example section, according to an illustrative embodiment.

DETAILED DESCRIPTION

Definitions

The term "glyceride oil" used herein refers to an oil or fat which comprises triglycerides as the major component thereof. For example, the triglyceride component may be at least 50 wt. % of the glyceride oil. The glyceride oil may also include mono- and/or di-glycerides. Glyceride oils include vegetable oils, marine oils and animal oils/fats which typically also include phospholipid components in their crude form.

The term "triglyceride" refers to a triester of glycerol with three fatty acid units. The fatty acid units present in the triglyceride may be the same as each other or they may be different.

The term "fatty acid" is used to refer to an aliphatic monocarboxylic acid have a chain of four to 28 carbons (usually unbranched and even numbered), which may be saturated or unsaturated (cis or trans, mono or polyunsaturated).

The term "hydrocarbon" refers to a class of compounds containing hydrogen bound to carbon, and encompasses (i) saturated hydrocarbon compounds, (ii) unsaturated hydrocarbon compounds, and (iii) mixtures of hydrocarbon compounds (saturated and/or unsaturated), including mixtures of hydrocarbon compounds having different numbers of carbon atoms.

The term "Cn" means hydrocarbon(s) having n carbon atom(s) per molecule, wherein n is a positive integer. As used herein, the term "Cn+" refers to a hydrocarbon composition defined by hydrocarbons having "n" or more carbon atoms, where "n" is an integer greater than 0. This includes paraffins, olefins, cyclic hydrocarbons, and aromatics and isomers thereof. Similarly, the term "Cn−" refers to a hydrocarbon composition defined by hydrocarbons having "n" or fewer carbon atoms, wherein "n" is an integer greater than 0. This includes paraffins, olefins, cyclic hydrocarbons, aromatics, and isomers thereof.

The term "light olefins" is used herein to designate olefins having 2 to 4 carbon atoms (e.g., ethylene, propylene and butylenes).

The term "large-pore" means a molecular sieve framework having a maximum ring size of at least 12 tetrahedral atoms, "medium-pore" means a molecular sieve framework having a maximum ring size of at least 10 tetrahedral atoms, and the term "small-pore" means a molecular sieve framework having a maximum ring size of at least 8 tetrahedral atoms.

The term "wt. %" refers to a weight percentage of a component based on the total weight of material that includes the component. In a non-limiting example, 10 grams of component in 100 grams of the material is 10 wt. % of component.

Glyceride Oil

The glyceride oil originates from renewable or biological source or sources, and it is meant to include here feedstock other than those obtained from crude oil (mineral oil) or shale oil or coal.

The glyceride oil may originate from plants, animals, algae, fish and microbiological processes.

The glyceride oil comprises at least 50 wt. % (at least 60 wt. %, at least 70 wt. %, at least 80 wt. %, at least 90 wt. %, or at least 95 wt. %) of triglycerides. The glyceride oil may also glyceride oil may also include mono- and/or di-glycerides, free fatty acids and other substances typically present at low levels in fats and oils derived from natural sources.

The glyceride oil may contain a single type of triglyceride, but more typically will contain a mixture of two or more different triglycerides.

Representative glyceride oils include rapeseed oil, colza oil canola oil, tall oil, sunflower oil, soybean oil, hempseed oil, cottonseed oil, corn oil, olive oil, linseed oil, mustard oil, palm oil, peanut oil, castor oil, coconut oil, *camellia* oil, *jatropha* oil, oils derived from microbial sources, which are possible genetically modified and includes at least algae, bacteria, molds and filamentous fungi; animal fats, fish oil, lard, tallow, train oil, recycled fats from the food industry and any mixture of the oils.

The glyceride oil may be pretreated to remove impurities to being contacted with the cracking catalyst. The pretreatment can include passing the glyceride oil through an adsorbent to remove metals, filtering the glyceride oil to remove sediment, or other processes.

Cracking Catalyst

The cracking catalyst of the present disclosure comprises at least 80 wt. % (e.g., at least 85 wt. %, at least 90 wt. %, at least 95 wt. %, or at least 99 wt. %) of a phosphorus-containing ZSM-5 light olefins additive.

Any conventional phosphorus-containing ZSM-5 light olefins additive typically used in an FCC process for light olefins production may be employed in the present disclosure.

The phosphorus-containing ZSM-5 light olefins additive may comprise (a) 25 to 50 wt. % (e.g., 40 to 50 wt. %) of ZSM-5 zeolite; (b) 3 to 15 wt. % (e.g., 5 to 10 wt. %) of phosphorus, measured as $P_2O_5$; (c) 5 to 40 wt. % (e.g., 10 to 20 wt. %) of a clay; and (d) 5 to 20 wt. % (e.g., 10 to 20 wt. %) of a binder.

The clay may be selected from the group consisting of kaolin, halloysite, bentonite, and any combination thereof. In some aspects, the clay is kaolin.

The binder may be selected from the group consisting of a silica sol, an alumina sol, pseudoboehmite alumina, bayerite alumina, gamma-alumina, and any combination thereof.

Examples of suitable P/ZSM-5 light olefins additives include those commercially available from Grace (e.g., OlefinsMax®, OlefinsUltra®, OlefinsUltra® HZ, OlefinsUltra® MZ and OlefinsUltra® XZ), Johnson Matthey (e.g., INTERCAT™, PENTACAT™ HP, PROPYL MAX™, SUPER Z™, SUPER Z EXCEL, SUPER Z EXCEED, ISOCAT™, and OCTAMAX™), and BASF (e.g., ZIP Olefins Additive).

The cracking catalyst may further comprise a large-pore molecular sieve component in addition to the phosphorus-containing ZSM-5 light olefins additive. The large-pore molecule sieve component may comprise, for example, a *BEA framework type zeolite (e.g., Beta zeolite) and/or a FAU framework type zeolite (e.g., Y zeolite). When used, the large-pore molecular sieve component is typically present in an amount of no more than 20 wt. % (e.g., 0.1 to 20 wt. %, or 1 to 15 wt. %), based on the weight of the cracking catalyst. Optionally, the additional molecular sieve component may further comprise matrix, binder and/or clay.

The cracking catalyst may be in the form of shaped microparticles, such as microspheres. As described, "microparticles" refer to particles having of size of from 0.1 microns and 100 microns. The size of a microparticle refers to the maximum length of a particle from one side to another, measured along the longest distance of the microparticle.

The cracking catalyst may be deactivated by contact with steam prior to use in a reactor to convert the feedstock. The purpose of steam treatment is to accelerate the hydrothermal aging which occurs in an operational FCC regenerator to obtain an equilibrium catalyst. Steam treatment may lead to the removal of aluminum from the framework leading to a decrease in the number of sites where framework hydrolysis can occur under hydrothermal and thermal conditions. This removal of aluminum results in an increased thermal and hydrothermal stability in dealuminated zeolites. The catalyst may be subjected to steaming in an atmosphere of from 5% to 100% steam for at least 1 hour (e.g., 1 hour to 200 hours) at a temperature of at least 300° C. (e.g., 300° C. to 800° C.).

Catalytic Cracking

The catalytic process can be either fixed bed, moving bed or fluidized bed and the feedstock flow may be either concurrent or countercurrent to the catalyst flow. The present process is particularly applicable to fluid catalytic cracking (FCC) processes.

The process of the present disclosure is particularly applicable to fluid catalytic cracking (FCC), in which the cracking catalyst is typically a fine powder This powder is generally suspended in the feed and propelled upward in a reaction zone. The feedstock is admixed with the cracking catalyst to provide a fluidized suspension and cracked in an elongated reactor, or riser, at elevated temperatures to provide a mixture of lighter hydrocarbon products. The gaseous reaction products and spent catalyst are discharged from the riser into a separator (e.g., a cyclone unit) located within the upper section of an enclosed stripping vessel, or stripper, with the reaction products being conveyed to a product recovery zone and the spent catalyst entering a dense catalyst bed within the lower section of the stripper. In order to remove entrained hydrocarbons from the spent catalyst prior to conveying the latter to a catalyst regenerator unit, an inert stripping gas (e.g., steam) is passed through the catalyst bed where it desorbs such hydrocarbons conveying them to the product recovery zone. The fluidizable catalyst is continuously circulated between the riser and the regenerator and serves to transfer heat from the latter to the former thereby supplying the thermal needs of the cracking reaction which is endothermic.

Typically, FCC conversion conditions include a riser top temperature of from 450° C. to 650° C. (e.g., 450° C. to 600° C., or 500° C. to 575° C.); a pressure of from 100 kPa to 1100 kPa (e.g., 200 kPa to 400 kPa); a catalyst-to-oil mass ratio of from 3 to 12 (e.g., 4 to 11, or 5 to 10); and a catalyst residence time of from 0.1 to 15 seconds (e.g., 0.2 to 10 seconds). Suitable regeneration temperatures include a temperature ranging from 600° C. to 800° C. at a pressure ranging from 100 kPa to 1100 kPa.

A mineral oil component such as those typically derived from crude oil or shale oil that has optionally been subjected to one or more separation and/or other refining processes may be combined with the glyceride oil feedstock. However, given the differing cracking characteristics of glyceride oil and mineral oil feedstocks, it is normally preferred to carry out the cracking in a unit dedicated to biofeed cracking, i.e., with a feedstock comprised entirely of biocomponent(s).

The product stream, comprising cracked renewable hydrocarbons, obtained from the cracking step may be separated into one or more hydrocarbon fractions using, for example, a fractionator. The product stream may include dry gases (e.g., one of more of hydrogen, methane, and ethane), liquefied petroleum gases (e.g., one or more of propane and butane), light olefins (e.g., one or more of ethylene, propylene, and butylenes), gasoline (boiling range of C5 to 221° C.), light cycle oil (boiling range of 221° C.+ to 343° C.) and heavy cycle oil (boiling range of 343° C.+ to final boiling temperature) Some heavier hydrocarbons may be recycled to the reactor.

In some aspects, the product stream may comprise from 30 wt. % to 60 wt. % (e.g., from 40 wt. % to 50 wt. %) of gasoline boiling range hydrocarbons, as determined by ASTM D2887. In some aspects, gasoline boiling range hydrocarbons may comprise at least 80 wt. % (e.g., at least 85 wt. %, or 85 wt. % to 95 wt. %) of C6 to C8 aromatic compounds. The obtained gasoline fraction may be useful as high quality renewable gasoline fuel and/or naphtha fuel, or as a blending component for these fuels.

In some aspects, the product stream may comprise xylenes with a para-xylene selectivity of from 50% to 99.9% (e.g., 60% to 80%) within the xylene fraction. Of the xylene isomers, para-xylene is of particular value since it is useful in the manufacture of terephthalic acid, which is an intermediate in the manufacture of synthetic fibers and resins.

In some aspects, the product stream may comprise at least 25 wt. % (25 wt. % to 40 wt. %, or 30 wt. % to 40 wt. %) of light olefins, as determined by ASTM D2887. Renewable C3 and C4 product olefins can be directed to a petrochemical unit or to an alkylation unit to produce a high octane gasoline by the reaction of an isoparaffin (e.g., isobutane) with one or more of the light olefins (usually propylene and butylene). Renewable ethylene product can be directed to a petrochemical unit for further processing.

Hydrocarbon fractions may undergo further processing before commercial use. Examples of such processing may include hydroprocessing and addition of additives.

EXAMPLES

The following illustrative examples are intended to be non-limiting.

Example

A series of laboratory tests were carried out to study the cracking of soybean oil or a vacuum gas oil (VGO) under FCC conditions using three different catalysts: a commercial phosphorus containing ZSM-5 based FCC additive, a spent FCC equilibrium catalyst (FCC ECAT) and a 50/50 mixture of ZSM-5 additive and FCC ECAT by weight. The spent FCC ECAT was obtained from an FCC unit processing hydrotreated feed and had a total metals (Ni+V) content of less than 500 ppm, a total surface area of 185 m²/g, and a unit cell size of 24.34 Å. Prior to use, the ZSM-5 additive was subjected to 50% steam treatment at 800° C. for 24 hours.

Catalytic cracking experiments were carried out using an Advanced Cracking Evaluation (ACE) Model C unit fabricated by Kayser Technology. A schematic diagram of the ACE Model C unit is shown in FIG. 1. The reactor employed in the ACE unit was a fixed fluidized reactor with 1.6 cm ID. Nitrogen was used as fluidization gas and introduced from both bottom and top. The top fluidization gas was used to carry the feed injected from a calibrated syringe feed pump via a three-way valve. The catalytic cracking of the feed was carried out at atmospheric pressure and 975° F. For each experiment, a constant amount of feed was injected at the rate of 1.2 g/min for 75 seconds. The catalyst-to-oil mass ratio was maintained at 7 for each catalyst tested. After 75 seconds of feed injection, the catalyst was stripped off by nitrogen for a period of 525 seconds.

During the catalytic cracking and stripping process, the liquid product was collected in a sample vial attached to a glass receiver, which was located at the end of the reactor exit and was maintained at −15° C. The gaseous products were collected in a closed stainless-steel vessel (12.6 L) prefilled with $N_2$ at 1 atm. Gaseous products were mixed by an electrical agitator rotating at 60 rpm as soon as feed injection was completed. After stripping, the gaseous products were further mixed for 10 mins to ensure homogeneity. The final gaseous products were then analyzed using a refinery gas analyzer (RGA).

After the completion of stripping process, in-situ catalyst regeneration was carried out in the presence of air at 1300° F. The regeneration flue gas passed through a catalytic converter packed with CuO pellets (LECO Inc.) to oxidize CO to $CO_2$. The regeneration flue gas was then analyzed by an online infrared (IR) analyzer located downstream from the catalytic converter. Coke deposited during cracking process was calculated from the $CO_2$ concentrations measured by the IR analyzer.

As mentioned above, gaseous products, mainly C1 to C7 hydrocarbons, were resolved in an RGA. The RGA is a customized Agilent 7890B gas chromatograph (GC) equipped with three detectors, a flame ionization detector for hydrocarbons and two thermal conductivity detectors for nitrogen and hydrogen. A methanizer was also installed on the RGA to quantify trace amount of CO and $CO_2$ in the gas products. Gas products were grouped into dry gas (C2− hydrocarbons and $H_2$) and liquefied petroleum gas (C3 and C4 hydrocarbons). CO and $CO_2$ were excluded from dry gas. Liquid products were weighed and analyzed in a simulated distillation GC (Agilent 6890) using ASTM D2887. The liquid products were cut into gasoline (C5 to 430° F.), light cycle oil (430° F.+ to 650° F.) and heavy cycle oil (650° F.+). Gasoline (C5+hydrocarbons) in the gaseous products were combined with gasoline in the liquid products as total gasoline. Light ends in the liquid products (C5−) were also subtracted from liquid products and added back to C3 and C4 species using some empirical distributions. Material balances were between 98% and 101% for most experiments.

Detailed hydrocarbon analysis (DHA) using Agilent 6890A (Separation Systems Inc.) were also performed on the gasoline portion of liquid products for PONA (paraffins, olefins, naphthenes, and aromatics) and octanes (RON and MON). DHA analysis on the gasoline portion in gaseous products was not performed. Therefore, the adjustment to total gasoline properties was not performed. Nevertheless, the DHA results still provided valuable information to evaluating catalytic cracking product properties.

TABLE 1

Catalytic Cracking of Soybean Oil and VGO

| | Catalyst | | | |
|---|---|---|---|---|
| | ZSM-5 Additive | ZSM-5/ FCC ECAT | FCC ECAT | ZSM-5 |
| Feed | Soybean Oil | Soybean Oil | Soybean Oil | Additive VGO |
| Conversion [wt. %] | 94.70 | 90.90 | 82.90 | 19.40 |
| Product Yield [wt. %] | | | | |
| Coke | 0.88 | 4.98 | 6.18 | 1.96 |
| Dry Gas | 5.45 | 4.03 | 2.13 | 2.13 |
| Ethane | 0.22 | 0.41 | 0.55 | 0.30 |
| Ethylene | 5.04 | 3.17 | 0.92 | 1.52 |
| Propane | 2.38 | 1.66 | 1.50 | 1.00 |
| Propylene | 13.44 | 11.35 | 5.24 | 3.27 |
| n-Butane | 0.87 | 0.73 | 1.05 | 0.33 |

TABLE 1-continued

Catalytic Cracking of Soybean Oil and VGO

| | Catalyst | | | |
|---|---|---|---|---|
| | ZSM-5 Additive | ZSM-5/ FCC ECAT | FCC ECAT | ZSM-5 |
| Isobutane | 1.15 | 4.07 | 3.90 | 0.35 |
| C4 Olefins | 10.88 | 8.79 | 4.49 | 2.21 |
| C5 Olefins | 4.96 | 4.59 | 2.83 | 0.93 |
| Gasoline | 46.85 | 42.25 | 46.00 | 8.20 |
| Gasoline Aromatics [%] | 89.50 | 78.00 | 61.00 | — |
| Gasoline Isoparaffins [%] | 1.20 | 7.20 | 19.30 | — |
| para-Xylene Selectivity [%] | 76 | 45 | 17 | — |

The results show that, for the catalytic cracking of soybean oil, the conversion and yields of light olefins as well as gasoline aromatics increased as the amount of P/ZSM-5 additive in the cracking catalyst formulation increased. Lower conversion and yields of light olefins and gasoline were observed when cracking a VGO feedstock with the P/ZSM-5 additive. Without being bound by theory, it is believed that the pore size of ZSM-5 limits the accessibility of active sites to the VGO feed molecules.

The invention claimed is:

1. A process for catalytic cracking of a feedstock consisting of glyceride oils, the process comprising:
(a) catalytically cracking the feedstock consisting of glyceride oils in the presence of a single catalyst at catalytic cracking conditions to obtain a product stream comprising hydrocarbons; and
(b) separating one hydrocarbon fraction from the product stream: wherein the single catalyst consists of:
(i) 25 to 50 wt. % of ZSM-5;
(ii) 3 to 15 wt. % of phosphorus, measured as $P_2O_5$;
(iii) 5 to 45 wt. % of a clay;
(iv) 5 to 20 wt. % of a binder; and
wherein the process is a fluid catalytic cracking process.

2. The process of claim 1, wherein at least 80 wt. % of glyceride oils are triglycerides.

3. The process of claim 1, wherein the glyceride oil is selected from rapeseed oil, colza oil canola oil, tall oil, sunflower oil, soybean oil, hempseed oil, cottonseed oil, corn oil, olive oil, linseed oil, mustard oil, palm oil, peanut oil, castor oil, coconut oil, *camellia* oil, *jatropha* oil, a microbial oil, animal fats, fish oil, lard, tallow, train oil, recycled fats from the food industry, and any combination thereof.

4. The process of claim 1, wherein the catalytic cracking conditions include a temperature of from 450° C. to 650° C.; a pressure of from 100 kPa to 1100 kPa; and a catalyst-to-oil mass ratio of from 3 to 12.

5. The process of claim 1, further comprising fractionating the product stream into one or more hydrocarbon fractions.

6. The process of claim 5, the one or more hydrocarbon fractions is selected from light olefins and gasoline.

* * * * *